United States Patent [19]

Glabiszewski

[11] Patent Number: 5,443,530
[45] Date of Patent: Aug. 22, 1995

[54] ELBOW FITTING PART

[75] Inventor: Richard Glabiszewski, Duderstadt Ot Westerode, Germany

[73] Assignee: Otto Bock Orthopaedische Industrie Besitz- und Verwaltungs-Kommanditgesellschaft, Duderstadt, Germany

[21] Appl. No.: 78,301

[22] PCT Filed: Oct. 26, 1992

[86] PCT No.: PCT/DE92/00891

§ 371 Date: Jun. 25, 1993

§ 102(e) Date: Jun. 25, 1993

[87] PCT Pub. No.: WO93/07836

PCT Pub. Date: Apr. 29, 1993

[30] Foreign Application Priority Data

Oct. 25, 1991 [DE] Germany .............. 41 35 229.7

[51] Int. Cl.$^6$ .............................. A61F 2/56; A61F 2/58
[52] U.S. Cl. .......................................... 623/59; 623/33
[58] Field of Search ............................. 623/57–60, 623/33

[56] References Cited

U.S. PATENT DOCUMENTS

| | | |
|---|---|---|
| 2,033,150 | 3/1936 | Radtke . |
| 2,537,338 | 1/1951 | Fishbein et al. . |
| 2,572,914 | 10/1951 | Chapman et al. . |
| 2,812,961 | 11/1957 | Brown et al. ............... 287/14 |
| 2,944,846 | 7/1960 | Jones ...................... 623/57 X |
| 3,526,007 | 9/1970 | Ivko et al. ................. 623/60 X |
| 3,833,942 | 9/1974 | Collins ...................... 623/60 |
| 5,007,937 | 4/1991 | Fishman et al. ............. 623/34 |
| 5,139,526 | 8/1992 | Skardoutos et al. .......... 623/59 |

FOREIGN PATENT DOCUMENTS

| | | |
|---|---|---|
| 1061971 | 4/1954 | France . |
| 415916 | 7/1925 | Germany . |
| 1268782 | 5/1968 | Germany . |
| 7013277 | 3/1982 | Taiwan . |
| 7027066 | 11/1982 | Taiwan . |
| 182670 | 7/1922 | United Kingdom . |
| 0376874 | 7/1932 | United Kingdom ........... 623/57 |
| 0158382 | 1/1963 | U.S.S.R. ..................... 623/58 |
| 0982688 | 12/1982 | U.S.S.R. ..................... 623/59 |

*Primary Examiner*—David H. Willse
*Attorney, Agent, or Firm*—Foley & Lardner

[57] ABSTRACT

An elbow fitting part for upper arm stumps includes an elbow ball connected by a hinged axle to the lower arm, configured as a hollow synthetic part, and is detainable by a latch-locking device in various bending positions, while the proximal connection to the upper arm shaft is created by a cast-in ring and an upper arm rotating joint is provided for the adjustable rotation of the lower arm. In order to make this elbow fitting part usable for all upper arm stump lengths, the upper arm rotating joint is configured as an annual bearing and the latch-locking device is a traction lock which is disposed outside the elbow ball and is integrated into a rotating connection forming a section of the hinged axle.

9 Claims, 4 Drawing Sheets

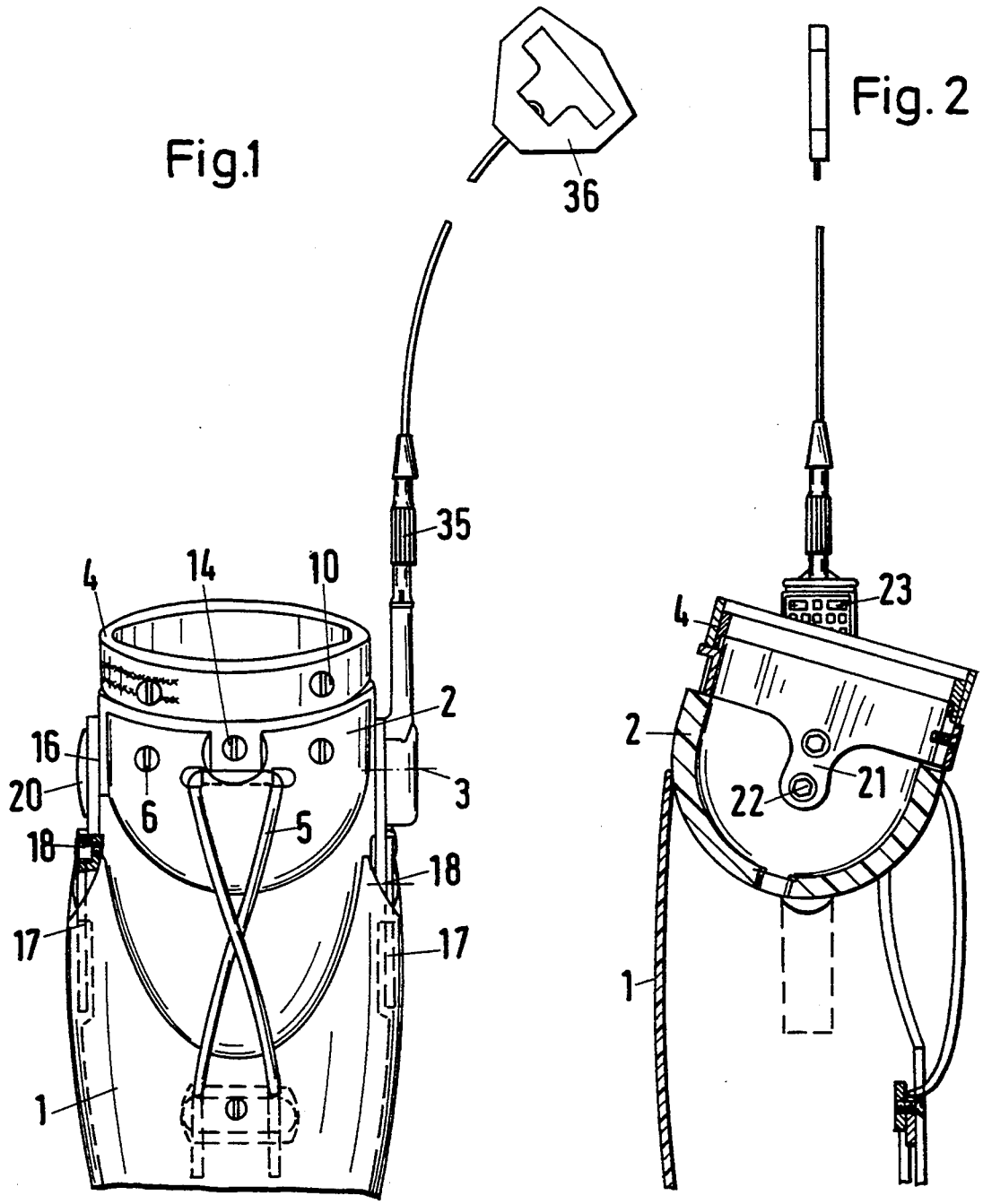

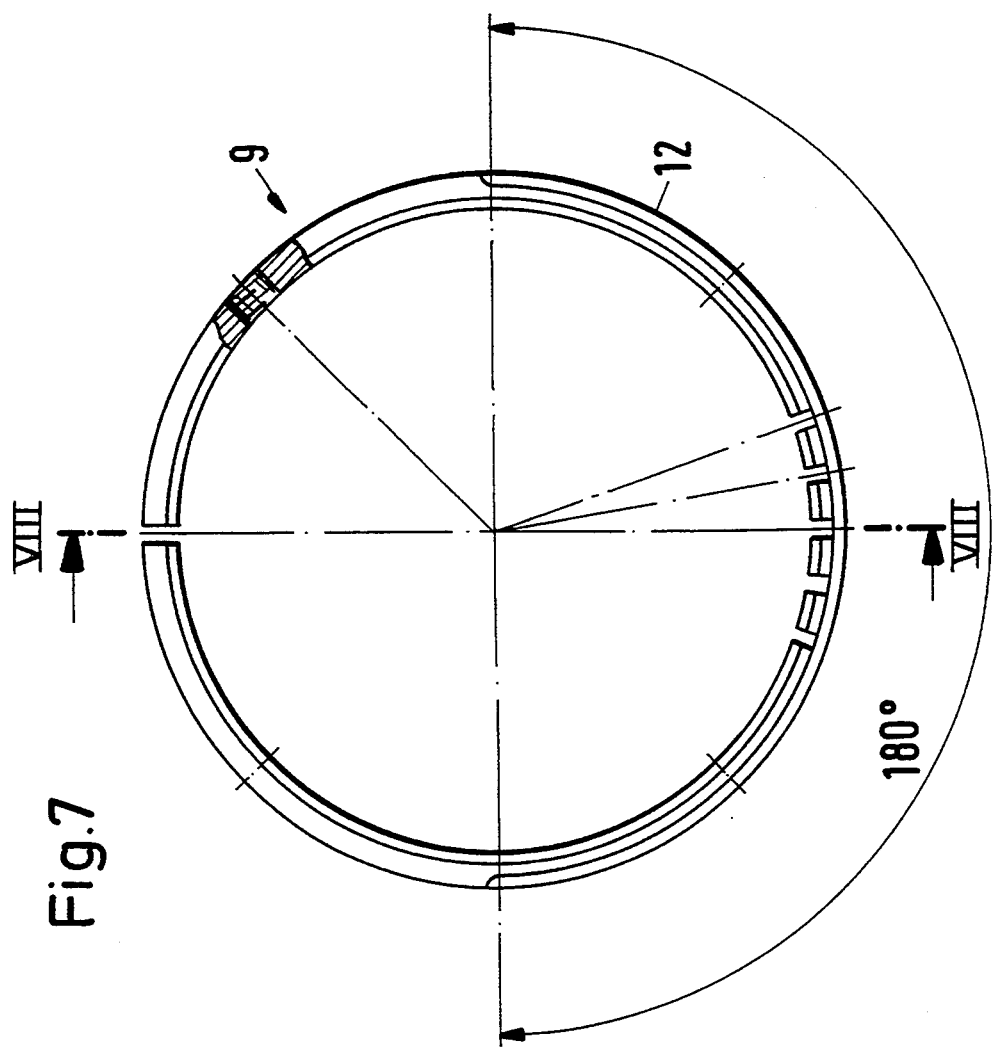

5,443,530

ELBOW FITTING PART

BACKGROUND OF THE INVENTION

The invention relates to an elbow fitting part for upper arm stumps, an elbow ball being connected by a hinged axle to the lower arm, configured as a hollow synthetic part, and being detainable by a latch-locking device in various bending positions, while the proximal connection to the upper arm shaft is created by means of a cast-in ring and an upper arm rotating Joint is provided for the adjustable rotation of the lower arm.

Known elbow fitting parts exhibit an upper arm rotating joint in the form of a sickle joint configured as a plane bearing and are therefore only suitable for limited upper arm stump lengths. In order to cater to long stumps, elbow fitting parts without a sickle Joint are used. Where these previously known elbow fitting parts exhibit a latch-locking device, this engages into a catch disposed on the outer periphery of the elbow ball.

SUMMARY OF THE INVENTION

The object of the invention is to design the elbow fitting part described in the introduction such that it is suitable for all upper arm stump lengths.

This object is achieved according to the invention by the fact that the upper arm rotating joint is configured as an annular bearing and the latch-locking device is a traction lock which is disposed outside the elbow ball and is integrated into a rotating connection forming a section of the hinged axle.

It is expedient, in this case, for the upper arm rotating Joint to comprise a bearing ring which is inserted into the elbow ball and is connected thereto in a rotationally secure manner and to exhibit an annular crosspiece which is embraced by a brake ring connected in a rotationally secure manner to the cast-in ring, the latter being twistable by 180° in relation to the bearing ring (7).

The measures according to the invention enable the needs of patients having any optional stump length up to elbow exarticulation to be met with only one rotating joint, for the configuration of the upper arm rotating joint as an annular bearing instead of the previously used plane bearing means that the necessary space is acquired for virtually any optional stump length. As a result of the externally disposed traction lock, the geometry for long stumps is guaranteed; no constructional adaptation to different stump lengths is necessary.

Further features form the subject of the subclaims and are explained in greater detail in connection with further advantages of the invention, with reference to an illustrative embodiment.

BRIEF DESCRIPTION OF THE DRAWINGS

One embodiment of the invention, serving as an example, is represented in the drawing, in which:

FIG. 1 shows an elbow fitting part in side view and partly in longitudinal section;

FIG. 2 shows the representation according to FIG. 1 rotated by 90° and in longitudinal section;

FIG. 7 shows a brake ring in top view and

FIG. 8 shows a section view taken along the line VIII—VIII in FIG. 7.

DETAILED DESCRIPTION OF A PREFERRING EMBODIMENT

Figure 3:
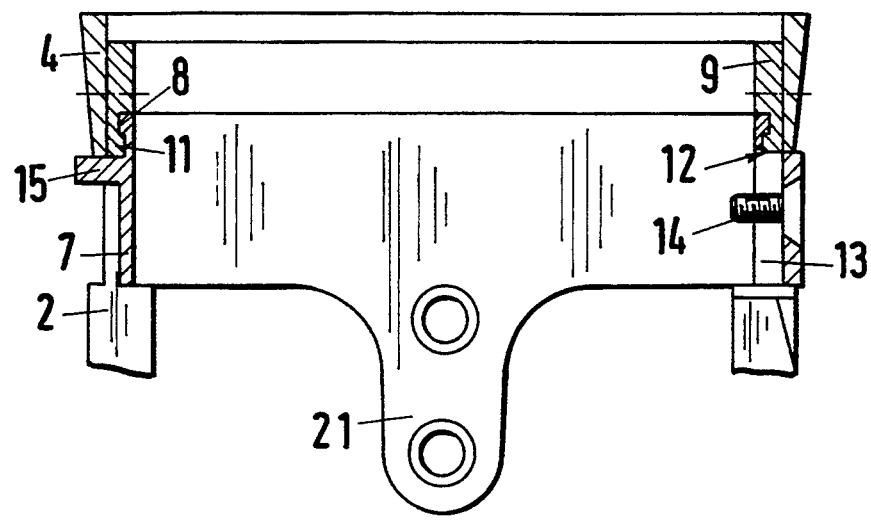
FIG. 3 shows, on an enlarged scale, a detail from FIG. 2.

The elbow fitting part represented in FIGS. 1 and 2 essentially comprises a lower arm 1, which is configured as a hollow synthetic part and at whose upper end an elbow ball 2 is mounted pivotably about a hinged axle 3 and can be detained in various bending positions by a latch-locking device. For the proximal connection to an upper arm shaft (not represented), a cast-in ring 4 is provided, which is part of an upper arm rotating joint for the adjustable rotation of the lower arm 1. When the lower arm 1 swings freely, the extension is limited by a front stop which is made of Perlon wire 5 and which is fastened on the one hand to the elbow ball 2 and on the other hand to the lower arm 1.

The upper arm rotating joint comprises a bearing ring 7, which is inserted into the elbow ball 2 and is connected thereto in a rotationally secure manner by means of screws 6 and exhibits an annular crosspiece 8, which is embraced by a brake ring 9 connected in a rotationally secure manner to the cast-in ring 4 by means of screws 10. The brake ring 9 is of slotted configuration and can thus be mounted onto the said annular crosspiece 8. The annular edge 11, facing the elbow ball 2, of the brake ring 9 exhibits a chamfering 12 over 180 peripheral degrees, against which chamfering a braking piece 13, consisting for example of a nonferrous metal, can be braced radially by means of a screw connection 14 which is accessible from the outside. The braking force exerted upon the brake ring 9 can be reset by adjustment of the screw connection 14.

The bearing ring 7 overlaps the elbow ball 2 by an annular flange 15, on which there is supported the cast-in ring 4 (see in particular FIGS. 2 and 3), which can be twisted by virtue of the chamfering 12 of the brake ring 9 and hence by 180°.

Figure 4:
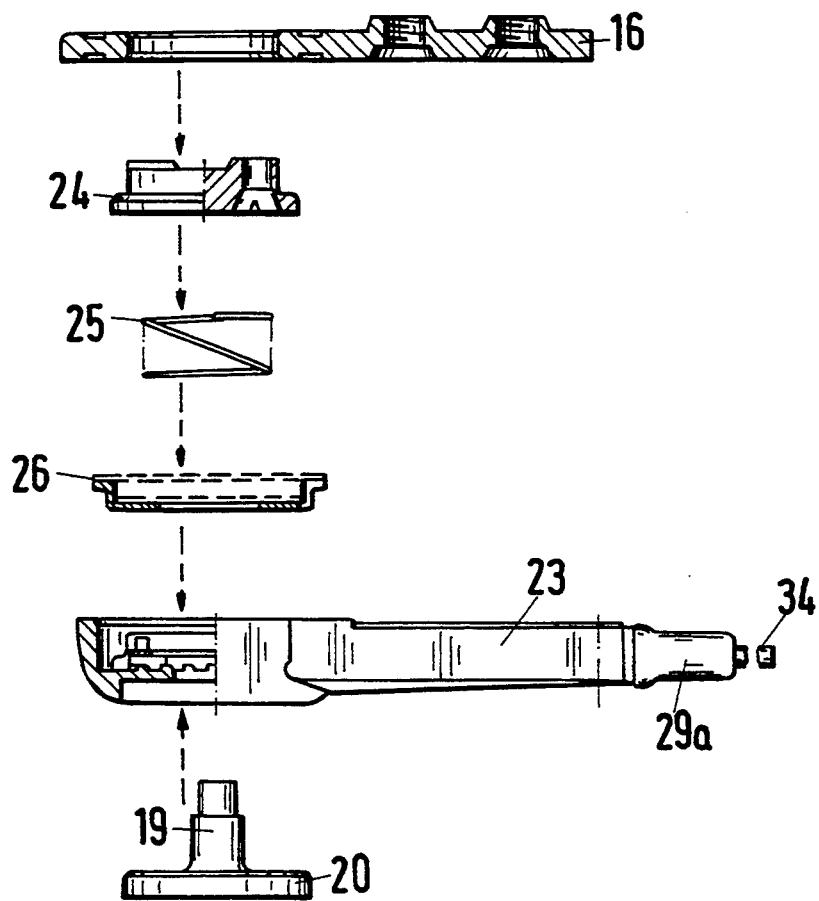
FIG. 4 shows, in exploded representation, a traction lock assembly.
Figure 6:
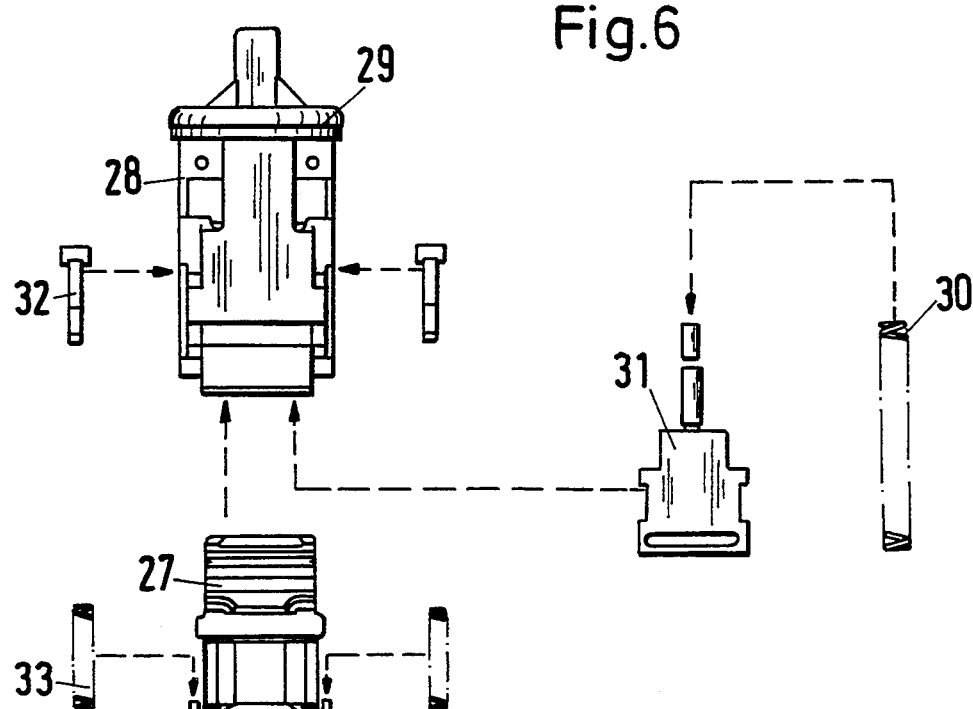
FIG. 6 shows, in exploded representation, a further assembly of the traction lock according to FIG. 5.
Figure 5:
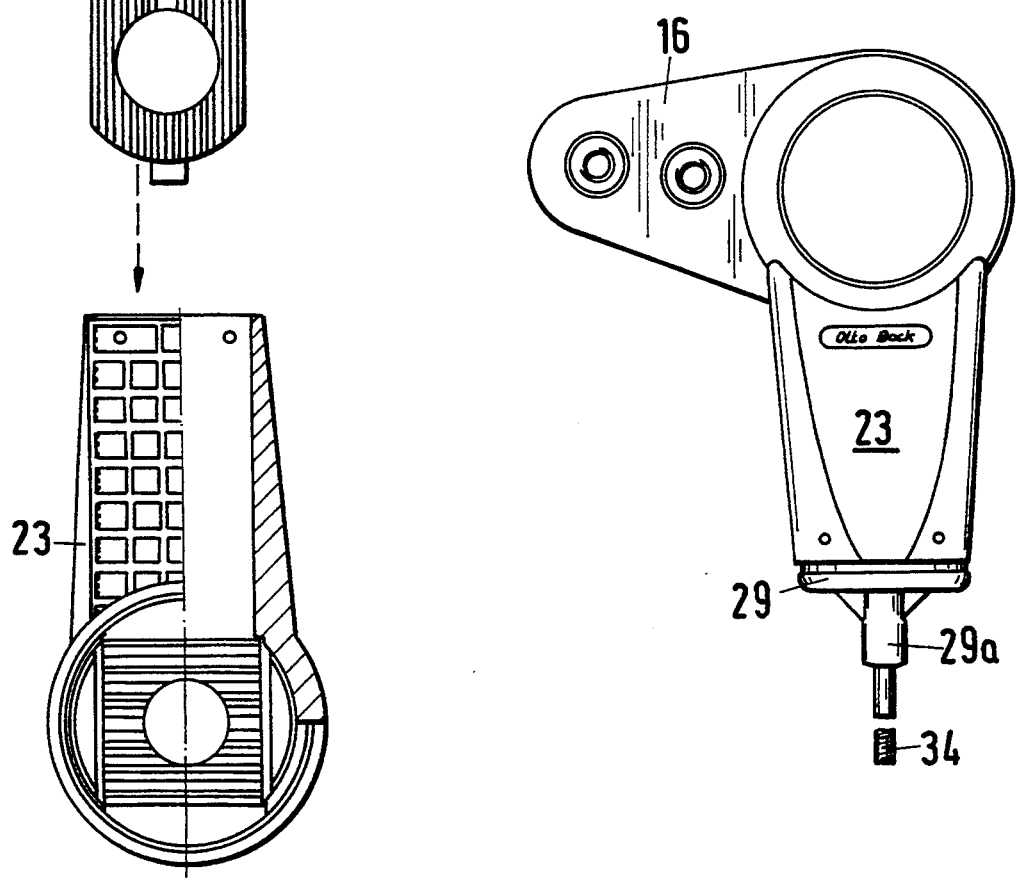
FIG. 5 shows, in top view, a traction lock linked to a hinged plate bar.

The hinged axle 3 is formed by two mutually aligned rotating connections, by means of which the elbow ball 2 is mounted pivotably between two hinged plate bars 16 which are firmly connected by means of screws 18 to lateral rails 17 integrated into the lower arm 1. Each rotating connection exhibits a hinge pin 19, which bears by means of a head 20 externally against the assigned hinged plate bar 16 (latch-free rotating connection) or against a housing 23 of the latch-locking device and is screw-connected (screws 22) by its other end to a lug 21 of the bearing ring 7. Outside the elbow ball 2, a latch-locking device in the form of a traction lock is integrated into the one rotating connection forming the hinged axle 3. The latch-locking device is mounted, with the housing 23, on the assigned hinged plate bar 16 such that it can be twisted on the one hinge pin 19, as is shown by FIG. 5. According to the exploded representation in FIG. 4, the housing 23 and the hinged plate bar 16 enclose between them a dog 24, a pressure spring 25, a latch disk 26 and a switch spring 27 (see FIG. 6).

Incorporated into the housing 23 is a drawer 28, which closes off the housing 23 by means of a flange 29 and comprises a wedge 31, the wedge being displaceable counter to the action of a pressure spring 30 and actuating pawls 32 which are acted upon by pressure springs 33. Assigned to the wedge 31 is the switch spring 27.

The wedge 31 exhibits at its one end a threaded pin 34, which is placed through the flange 29 and through a thereto attached connecting piece 29a of the drawer 28. Onto this threaded pin 34 there is screwed a traction cable 35 (represented in FIGS. 1 and 2), to whose free end there is fastened a clamp 36 for the manual actuation of the traction lock.

The traction lock can be released by tightening of the clamp 36; the elbow ball 2 is freely pivotable between the hinged plate bars 16 in relation to the lower arm 1. Renewed tightening of the clamp 36 produces a latch-locking of the elbow ball 2 in the desired bending position, eighteen latch-locking positions, for example, being able to be provided.

I claim:

1. An elbow fitting part for an upper arm stump comprising:
   an elbow ball connected by a hinged axle to a lower arm, configured as a hollow synthetic part, and being detainable by a latch-locking device in various bending positions, wherein a proximal connection to the upper arm stump includes a cast-in ring and an upper arm rotating joint provided for an adjustable rotation of the lower arm,
   wherein the upper arm rotating joint is configured as an annular bearing and the latch-locking device is a traction lock which is disposed outside the elbow ball and is integrated into a rotating connection forming a section of the hinged axle;
   wherein the upper arm rotating joint comprises a bearing ring which is inserted into the elbow ball and is connected thereto in a rotationally secure manner and which includes an annular crosspiece, the annular crosspiece being embraced by a brake ring connected in a rotationally secure manner to the cast-in ring, and the cast-in ring being twistable by 180° in relation to the bearing ring;
   wherein the brake ring can be acted upon by a braking piece;
   wherein an annular edge, facing the elbow ball, of the brake ring is acted upon by the braking piece; and
   wherein the braking piece bears against a chamfering of the annular edge of the brake ring, which chamfering extends over 180 peripheral degrees and defines a pivotal range of the cast-in ring.

2. An elbow fitting part according to claim 1, wherein the brake ring is slotted.

3. An elbow fitting part according to claim 1, wherein the braking piece can be braced radially against the brake ring by a screw connection which is accessible from the outside.

4. An elbow fitting part according to claim 1, wherein the bearing ring overlaps the elbow ball by an annular flange, which supports the cast-in ring.

5. An elbow fitting part according to claim 1, wherein the hinged axle is formed by two mutually aligned rotating connections, by means of which the elbow ball is mounted pivotally between two hinged plate bars connected to the lower arm.

6. An elbow fitting part according to claim 5, wherein each rotating connection includes a hinge pin which is screw-connected by its innermost end to a lug of the bearing ring.

7. An elbow fitting part according to claim 1, wherein the traction lock is mounted, with a housing, such that the traction lock can be twisted on one hinge pin.

8. An elbow fitting part according to claim 7, wherein the housing and a hinged plate bar enclose between them a dog, a pressure spring, a latch disk and a switch spring.

9. An elbow fitting part according to claim 7, wherein a wedge is mounted in the housing so as to be displaceable counter to an action of a pressure spring, the wedge actuating pawls and supporting at its one end a threaded pin protruding out of the housing, onto which threaded pin a traction cable is screwed.

* * * * *